US011324386B2

(12) United States Patent
Meyer et al.

(10) Patent No.: US 11,324,386 B2
(45) Date of Patent: May 10, 2022

(54) AIRWAY MANAGEMENT AND VISUALIZATION DEVICE

(71) Applicant: The General Hospital Corporation, Boston, MA (US)

(72) Inventors: Mark Meyer, Boston, MA (US); Matthew Sigakis, Ann Arbor, MI (US)

(73) Assignee: The General Hospital Corporation, Boston, MA (US)

( * ) Notice: Subject to any disclaimer, the term of this patent is extended or adjusted under 35 U.S.C. 154(b) by 178 days.

(21) Appl. No.: 15/579,588

(22) PCT Filed: Jun. 8, 2016

(86) PCT No.: PCT/US2016/036343
§ 371 (c)(1),
(2) Date: Dec. 4, 2017

(87) PCT Pub. No.: WO2016/200874
PCT Pub. Date: Dec. 15, 2016

(65) Prior Publication Data
US 2018/0168433 A1 Jun. 21, 2018

Related U.S. Application Data

(60) Provisional application No. 62/172,613, filed on Jun. 8, 2015.

(51) Int. Cl.
*A61B 1/00* (2006.01)
*A61B 1/05* (2006.01)
(Continued)

(52) U.S. Cl.
CPC ...... *A61B 1/00016* (2013.01); *A61B 1/00029* (2013.01); *A61B 1/00052* (2013.01);
(Continued)

(58) Field of Classification Search
None
See application file for complete search history.

(56) References Cited

U.S. PATENT DOCUMENTS 4,273,112 A * 6/1981 Heine ............... A61B 1/07
362/572
4,556,052 A * 12/1985 Muller .............. A61B 1/267
600/193
(Continued)

FOREIGN PATENT DOCUMENTS

CN 102068231 A 5/2011
CN 202386668 U 8/2012
(Continued)

OTHER PUBLICATIONS

International Search Report and Written Opinion for international application No. PCT/US2016/036343 dated Sep. 1, 2016, 11 pages.
(Continued)

*Primary Examiner* — Timothy J Neal
(74) *Attorney, Agent, or Firm* — Quarles & Brady LLP

(57) ABSTRACT

A medical visualization platform including a base unit that includes a base unit connection mechanism, a processor, an electrical contact, a communication module, and a power source. A plurality of visualization attachments connect lo the base unit, and each visualization attachment is disposable and includes a visualization connection mechanism arranged to engage the base unit connection mechanism to provide movement of the connected visualization attachment relative to the base unit between a folded position and an engaged position. Each visualization attachment also includes attachment contacts that are in electrical communication with the electrical contact of the base unit while the visualization attachment is in the engaged position, and each of the visualization attachments includes either a video camera or a light source.

18 Claims, 18 Drawing Sheets

(51) Int. Cl.
*A61B 1/06* (2006.01)
*A61B 1/267* (2006.01)
*A61B 1/07* (2006.01)
*G02B 23/24* (2006.01)

(52) U.S. Cl.
CPC .......... *A61B 1/00101* (2013.01); *A61B 1/053* (2013.01); *A61B 1/0676* (2013.01); *A61B 1/0684* (2013.01); *A61B 1/267* (2013.01); *A61B 1/2676* (2013.01); *A61B 1/00045* (2013.01); *A61B 1/00103* (2013.01); *A61B 1/07* (2013.01); *G02B 23/2484* (2013.01)

(56) References Cited

U.S. PATENT DOCUMENTS

| | | | | |
|---|---|---|---|---|
| 7,338,440 | B1 * | 3/2008 | Smith | A61B 1/06 600/185 |
| 2003/0088156 | A1 | 5/2003 | Berci et al. | |
| 2006/0281971 | A1 * | 12/2006 | Sauer | A61B 34/20 600/109 |
| 2009/0209816 | A1 | 8/2009 | Nielsen et al. | |
| 2009/0247833 | A1 * | 10/2009 | Tanaka | G09B 23/285 600/188 |
| 2010/0152541 | A1 | 6/2010 | Tenger et al. | |
| 2010/0159434 | A1 | 6/2010 | Lampotang et al. | |
| 2010/0249513 | A1 | 9/2010 | Tydlaska | |
| 2010/0261968 | A1 * | 10/2010 | Nearman | A61B 1/00041 600/188 |
| 2011/0028790 | A1 | 2/2011 | Farr et al. | |
| 2011/0130632 | A1 * | 6/2011 | McGrail | A61B 1/00016 600/188 |
| 2011/0245609 | A1 * | 10/2011 | Laser | A61B 1/00052 600/109 |
| 2011/0319718 | A1 * | 12/2011 | Hakanen | A61B 1/267 600/193 |
| 2012/0071725 | A1 * | 3/2012 | Plevnik | A61B 1/00103 600/188 |
| 2012/0078050 | A1 * | 3/2012 | Schwartz | A61M 25/04 600/120 |
| 2013/0018227 | A1 * | 1/2013 | Schoonbaert | A61B 1/00052 600/188 |
| 2014/0275760 | A1 | 9/2014 | Lee et al. | |
| 2015/0080655 | A1 | 3/2015 | Peterson et al. | |

FOREIGN PATENT DOCUMENTS

| | | |
|---|---|---|
| CN | 203341712 U | 12/2013 |
| CN | 104055479 A | 9/2014 |
| CN | 204091936 U | 1/2015 |
| CN | 105581768 A | 5/2016 |
| GB | 2209944 A | 3/1990 |
| WO | WO 2014184795 A1 | 11/2014 |

OTHER PUBLICATIONS

European Patent Office, Extended European Search Report, Application No. 16808152.9, dated Dec. 10, 2018, 8 pages.
China National Intellectual Property Office. First Office Action for application 201680046570.1 dated Jul. 22, 2019. With associate translation.
China National Intellectual Property Office. Second Office Action for application 201680046570.1 dated Mar. 5, 2020. With associate translation.

* cited by examiner

AIRWAY MANAGEMENT AND VISUALIZATION DEVICE

CROSS-REFERENCE TO RELATED APPLICATIONS

This application is a U.S. National Phase of PCT Application No. PCT/US2016/036343 filed on Jun. 8, 2016 which claims the benefit of U.S. Provisional Patent Application 62/172,613 filed on Jun. 8, 2015, the entire contents of which are incorporated by reference herein.

BACKGROUND OF THE INVENTION

Embodiments of the invention relate to the field of health care. More particularly, some embodiments relate to Anesthesiology, airway management, and/or airway visualization devices, including, but not limited to, laryngoscopes, video laryngoscopes, bronchoscopes, video bronchoscopes, and fiber optic bronchoscopes.

SUMMARY OF THE INVENTION

Embodiments provide an airway management and visualization platform that includes a universal base unit. The universal base unit connects to a multitude of airway management tools. Airway management tools that connect to the universal base unit can include, but are not limited to, direct laryngoscopy, video laryngoscopy, pediatric video laryngoscopy, and fiberoptic bronchoscopy (as defined below) with options for wired and wireless video. Airway management tools include of a multitude of visualization attachments that connect to the universal base unit and utilize video and wireless technology as needed to assist the placement of a breathing tube into a patient's airway. Airway management tools are easily and quickly swapped to allow for rapid escalation of airway management technique for the anticipated or unanticipated difficult airway and allows both wired and wireless video based on user preference.

In some embodiments, the airway management and visualization platform can include two primary parts, a universal base handle unit and a visualization attachment that connect to the universal base handle unit. The visualization attachment can include or be embodied by a multitude of physical forms. Each different visualization attachment can have unique architectures and attributes that aid in the manipulation and visualization of soft tissue and airway structures in the patient airway. A single visualization attachment is chosen by the clinician and then connected to the base unit to create a single device that is used for visualization of airway structures.

In more detail, visualization attachments that connect to the universal base unit are constructed in a manner in which they may be disposable or non-disposable. Visualization attachments may be constructed in large, small and intermediate sizes for use in patients ranging from infant to adult.

In more detail, visualization attachments include, but are not limited to, the following: (a) Standard laryngoscope blade structures, where "blade" is defined as the part of the laryngoscope that is inserted into the patient's airway to manipulate soft tissue and airway anatomy to assist in viewing the larynx and glottis opening. Visualization attachments include any standard laryngoscope blade structures, curved, bent or straight. Visualization attachments include any standard laryngoscope blade structures used for direct, non-video assisted view of the patient airway (laryngoscopy). (b) Video laryngoscope blade structures, with integrated camera for video assisted laryngoscopy. (c) Small form factor adhesive camera for placement on a separate laryngoscope blade, including infant, child or adult laryngoscope blades, to convert any standard laryngoscope into a video laryngoscope. (d) Equivalent of a flexible fiberoptic bronchoscope for fiberoptic-assisted airway management, including a flexible tube with camera and light on the distal end. This flexible fiberoptic bronchoscope attachment includes controls at the proximal end to direct the flex of the distal end, and an attachment to the universal base unit for use as a handle that serves to provide additional functionality as a combined device. (e) Other airway visualization embodiments that may or may not include an integrated video camera and attach to the universal base unit of the present invention. (f) Other visualization embodiments that are similar in form and function to a flexible fiberoptic bronchoscope, specifically a controllable distal tip on a flexible tube, proximal controls, a handle, video imaging and light illumination in the direction of the controllable distal tip, and channels through the flexible shaft for purposes including but not limited to tool insertion, irrigation, and suction, where the distal tip is introduced into an orifice of the body and the operator utilizes the proximal controls to direct the light and imaging by manipulation of the distal tip through the proximal controls. These embodiments include, but are not limited to, endoscopes, including those specialized for esophagogastroduodenoscopy, enteroscopy, colonoscopy, sigmoidoscopy, cholangiopancreatography, rectoscopy, anoscopy, proctoscopy, rhinoscopy, pharyngoscopy, cystoscopy, ureteroscopy, gynoscopy including colposcopy, hysteroscopy, and falloposcopy, and other specialized uses of endoscopes. In In more detail, all visualization attachments are able to connect to the universal base unit. The universal base unit may connect wirelessly to a wireless capable device with a screen (e.g., a smartphone, a computer, a tablet or a wearable device) to display transmitted video content from a visualization attachment containing a camera. The universal base unit may also connect directly to a video display device, such as a monitor or screen, or device with a screen, such as a smartphone, tablet, or personal computer, to display video content from a visualization attachment containing a camera; the embodiment that connects directly to a video display device or device with screen may or may not include wireless connectivity.

In one embodiment, a medical visualization platform includes a base unit that includes a base unit connection mechanism, a processor, an electrical contact, a communication module, and a power source. A plurality of visualization attachments connect to the base unit, and each visualization attachment is disposable and includes a visualization connection mechanism arranged to engage the base unit connection mechanism to provide movement of the connected visualization attachment relative to the base unit between a folded position and an engaged position. Each visualization attachment also includes attachment contacts that are in electrical communication with the electrical contact of the base unit while the visualization attachment is in the engaged position, and each of the visualization attachments includes either a video camera or a light source.

The foregoing and other aspects and advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

DETAILED DESCRIPTION OF THE INVENTION

Figure 1:
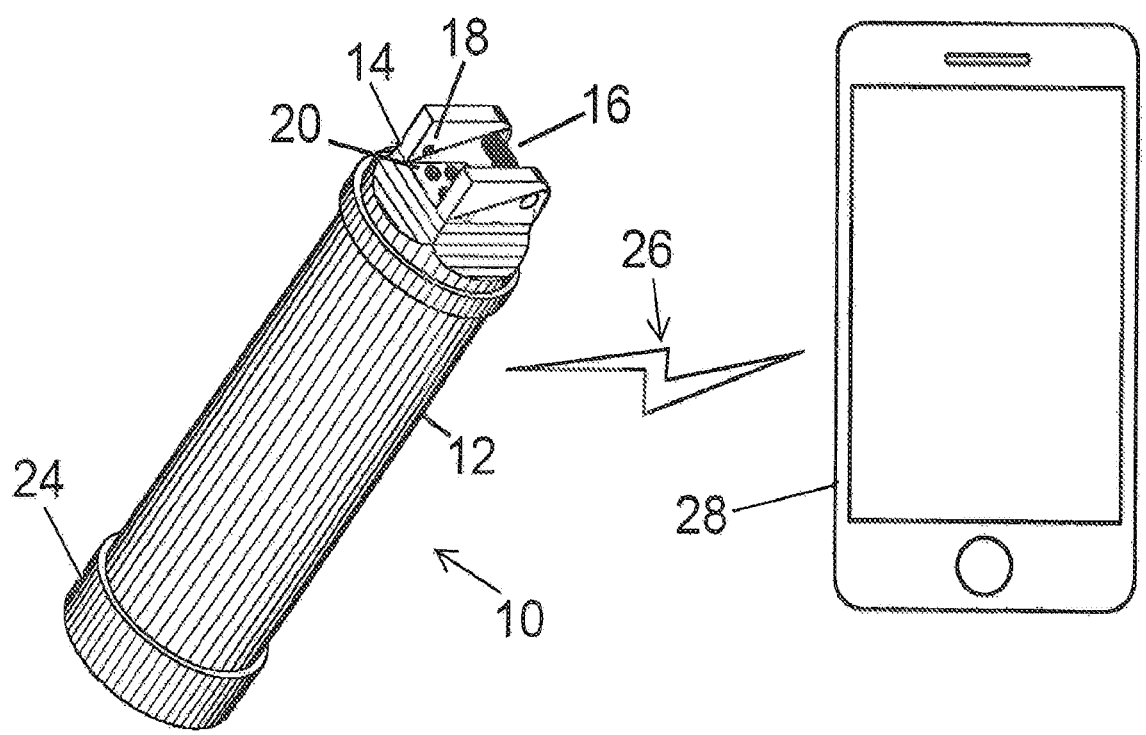
FIG. 1 is a perspective view of a base handle unit.

As shown in FIG. 1, a universal base unit 10 includes a grip 12 where a user holds the universal base unit 10, a cap 14 which provides a location where a visualization attachment (discussed below) will connect to the universal base unit 10, and a base 24.

As also shown in FIG. 1, the cap 14 includes a connection mechanism in the form of a horizontal cylindrical bar 16 that may be gripped by the visualization attachment and allow rotation about the horizontal cylindrical bar 16. The cap 14 further includes a detention mechanism in the form of a hemispherical depression 18, and electrical contacts or leads 20 arranged to provide electrical communication with the visualization attachment.

Figure 2:
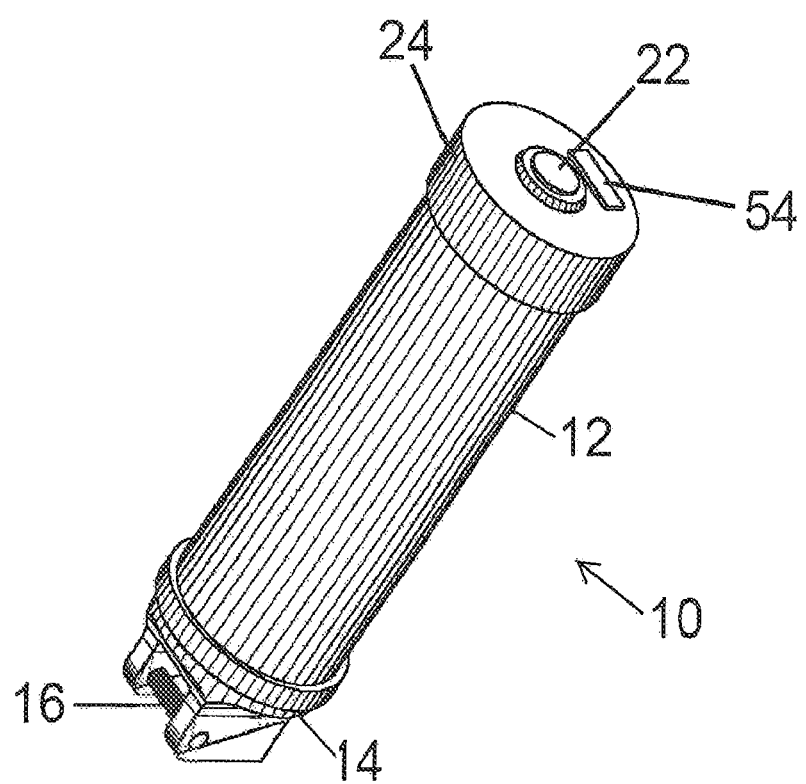
FIG. 2 is another perspective view of the base handle unit of FIG. 1.

As shown in FIG. 2, the base 24 includes a switch or button 22 that can be used to designate a specific functionality of the universal base unit 10 by the user, such as enabling wireless communication. A port or electrical connection 54 may be present on the universal base unit 10 so that a video display device may be directly connected to the universal base unit 10 and display video from the attached visualization component.

Figure 3:
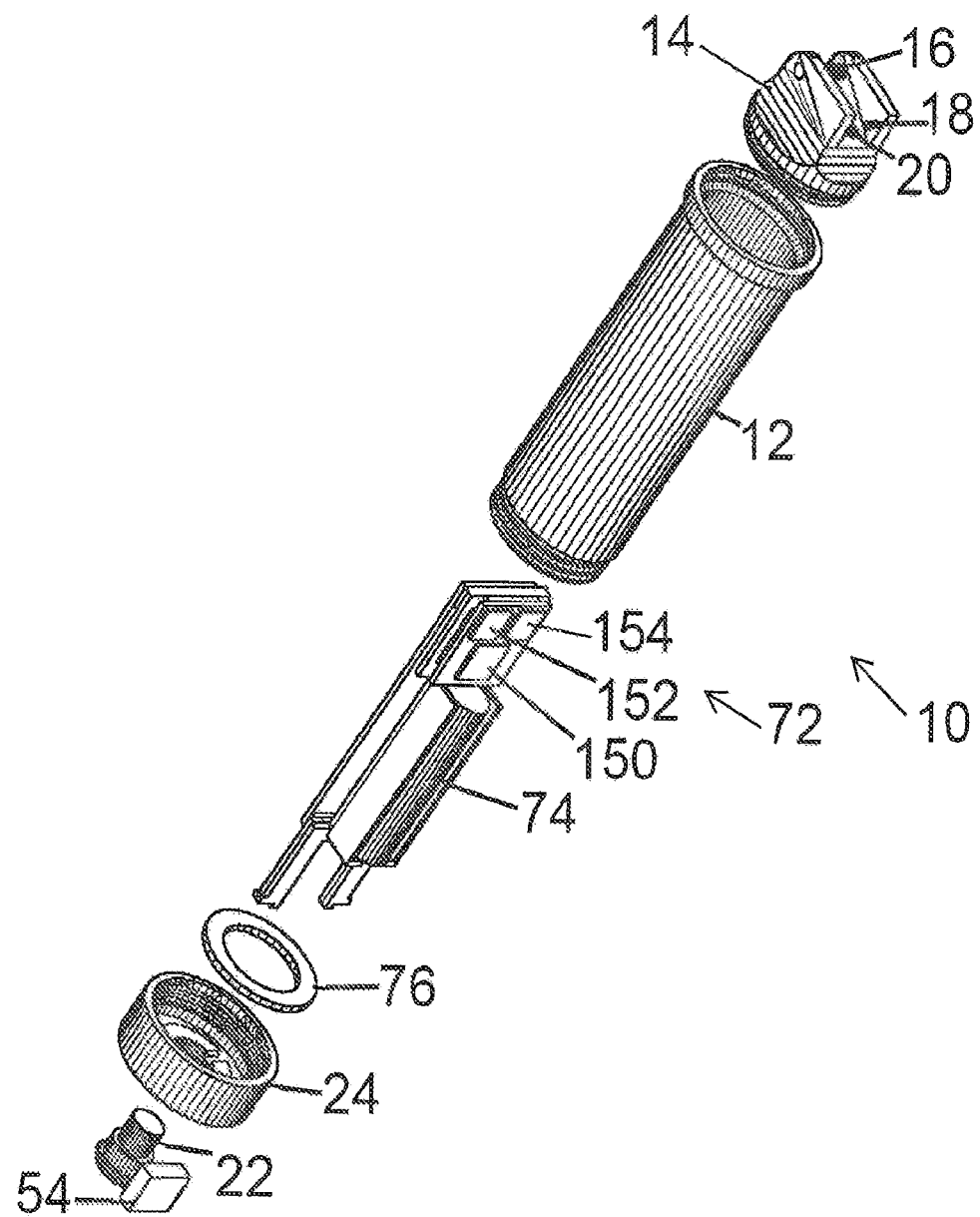
FIG. 3 is an exploded view of the base handle unit of FIG. 1.

As shown in FIG. 3, the universal base unit 10 includes an electrical system 72 housed within the grip 12. The electrical system 72 includes a battery 74, an induction charging coil 76, a microprocessor 150, a wireless communication chipset 152, and a power management component 154.

The microprocessor 150 may be utilized for functions including video processing, encoding and streaming. The wireless communication chipset 152 may function with 802.11, Bluetooth®, or another wireless communication protocol capable of streaming video. The wireless communication chipset 152 may be integrated into or with the microprocessor chip 150. The electronic system 72 includes power management for battery charging and voltage regulation 154. The battery 74 is a replaceable and/or rechargeable battery. Embodiments may include a replaceable battery, a rechargeable battery recharged by plugging the universal base unit 10 into a charging cable or unit, or as depicted in FIG. 3, the induction charging coil 76 can wirelessly recharge the battery 74. The electronic system 72 may include additional functionality through additional functions of the microprocessor 150 or additional chipsets, including but not limited to, location services such as radio-frequency identification or global positioning system, additional wireless communication protocols and chipsets for status broadcasting and updating such as low battery or maintenance needs, carbon dioxide detection, temperature, humidity, and other additional sensors.

In further detail, still referring to FIG. 3, the universal base unit 10 includes an area of sufficient length and circumference by which an individual may hold the universal base unit 10. The length of the grip 12 is at least the width of an average adult hand and the circumference of the grip 12 is of appropriate size to fit comfortably within an average-sized hand. The switch 22 is placed on the universal base unit 10 where it will not be inadvertently touched or altered while the universal base unit 10 is held. The battery 74 is of sufficient capacity to provide power to the electronic system 72 and any connected components for an adequate length of time. If present, the orientation of the induction coil 76 is such so that it closely mates with a corresponding coil in a charging device that is external to the universal base unit 10.

The universal base unit 10 may be made of plastic, metal, or any other sufficiently strong and rigid material. Further, the various components of the universal base unit 10 can be made of different materials.

In one embodiment, shown in FIG. 1, the universal base unit 10 connects wirelessly 26 to a wireless capable device 28 to display video from the attached visualization component.

Figure 4:
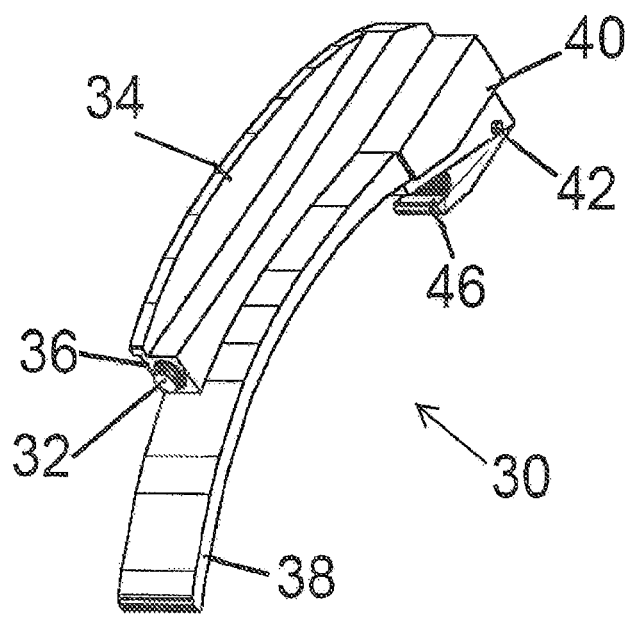
FIG. 4 is a perspective view of a visualization attachment in the form of a video laryngoscope blade with an integrated camera.
Figure 5:
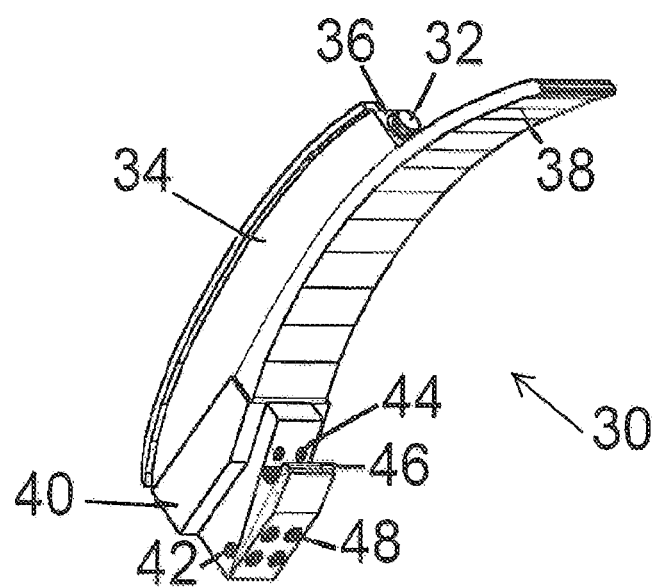
FIG. 5 is another perspective view of the video laryngoscope blade of FIG. 4.

As shown in FIG. 4 and FIG. 5, a visualization attachment in the form of a laryngoscope blade 30 includes a video camera 32 and a light 36 integrated into a body 34 of the blade. The body 34 houses the video camera 32 and the light 36 (e.g., a light emitting diode). The laryngoscope blade 30 also includes a tip 38 where the video camera 32 is directed, and a base 40 where the laryngoscope blade 30 connects to the universal base unit 10. The video camera 32 may optionally include as necessary a lens, a lens cover, an anti-fog cover, and a video encoding/processing microprocessor. The number of lights 36 is variable and equal to or greater than one. The number and strength of lights 36 is sufficient to adequately visualize the area of interest at the tip 38 of the blade 30.

Figure 8:
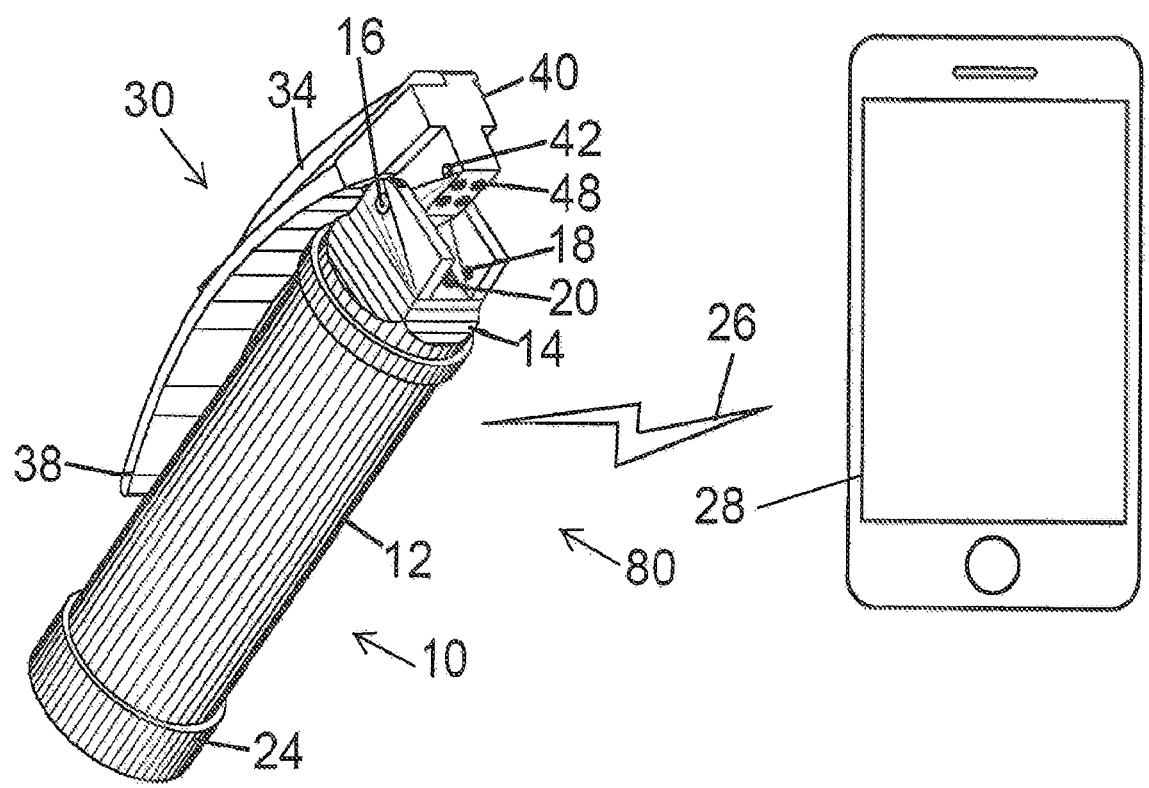
FIG. 8 is a perspective view of the base handle unit and a visualization attachment in the form of a laryngoscope blade in a first position.
Figure 9:
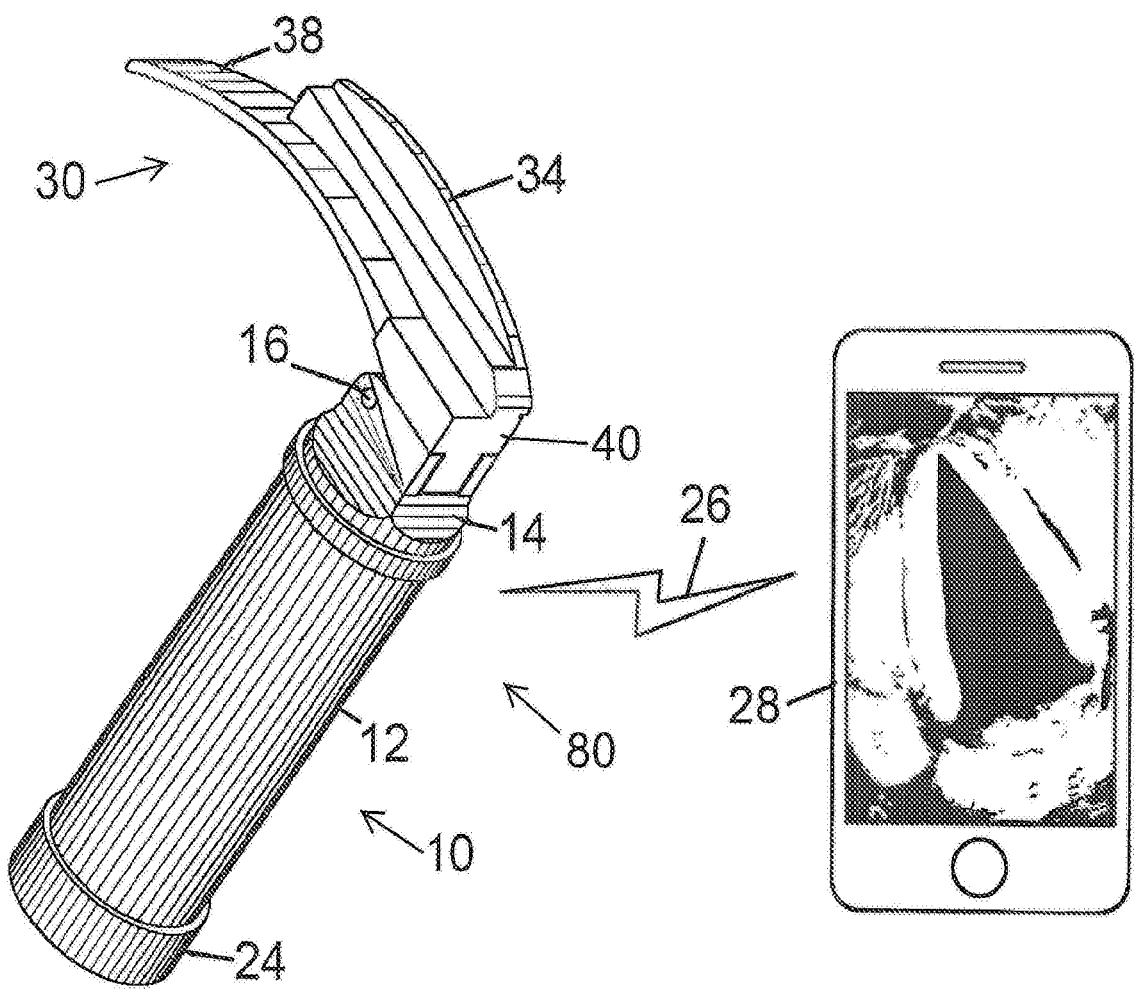
FIG. 9 is a perspective view of the base handle unit and the visualization attachment of FIG. 8 in a second position.

As further shown in FIGS. 4 and 5, the base 40 includes a mechanism in the form of a hemisphere protuberance 42 on the base 40 that is arranged to be captured by the hemisphere depression 18 on the cap 14 of the universal base unit 10, a mechanism in the form of one or several small protuberances 44, and a mechanism in the form of a groove 46 sized to engage the horizontal cylindrical bar 16 on the universal base unit 10 where the bar 16 may be pushed into the groove 46 and held in the groove 46 by the one or several small protuberances 44 to secure the laryngoscope blade 30 to the universal base unit 10 while allowing it to rotate between a first or folded position (shown in FIG. 8) and second or engaged position (shown in FIG. 9). In other embodiments, the mechanisms (e.g., 42, 44, and 46) may be designed differently to provide movement of a visualization attachment relative to the base unit 10. For example, a threaded connection, a prong and socket, a latched configuration, or other solutions exist for attaching the visualization device to the base unit 10.

As shown in FIG. 5, the base 40 of the laryngoscope blade 30 includes leads 48 that are arranged to mate with the leads 20 on the universal base unit 10 in the engaged position and also connect to the video camera 32 and light 36 through wires that run through the base 40 and body 34 of the laryngoscope blade 30.

As also shown in FIGS. 4 and 5, the laryngoscope blade 30 is of a comparable size to standard laryngoscope blades, and exists in adult and pediatric sizes. The geometry of the blade may be altered while grossly maintaining a similar form.

The laryngoscope blade 30 may be made of plastic, metal, or any other sufficiently strong and rigid material. Further, the various components of the laryngoscope blade 30 can be of different materials. The video camera 32 may be of low to moderate resolution to limit cost and allow the laryngoscope blade 30 to be considered a disposable unit, yet of sufficient resolution to provide clear visualization of anatomical structures.

Figure 6:
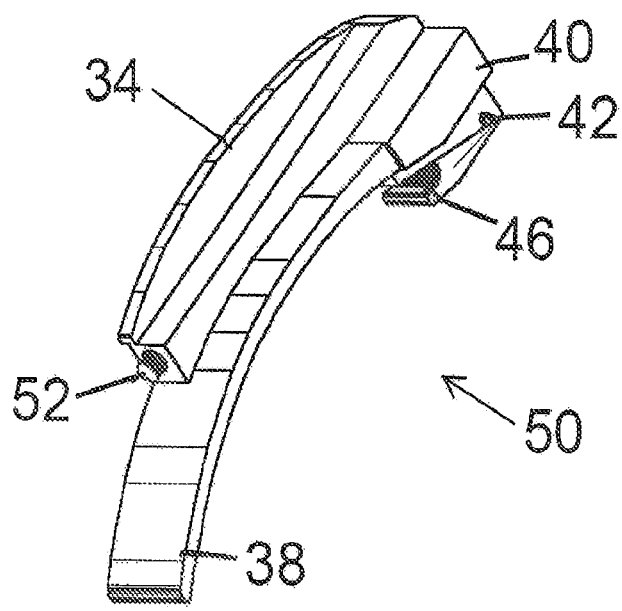
FIG. 6 is a perspective view of another visualization attachment in the form of a standard laryngoscope blade with a light source.
Figure 7:
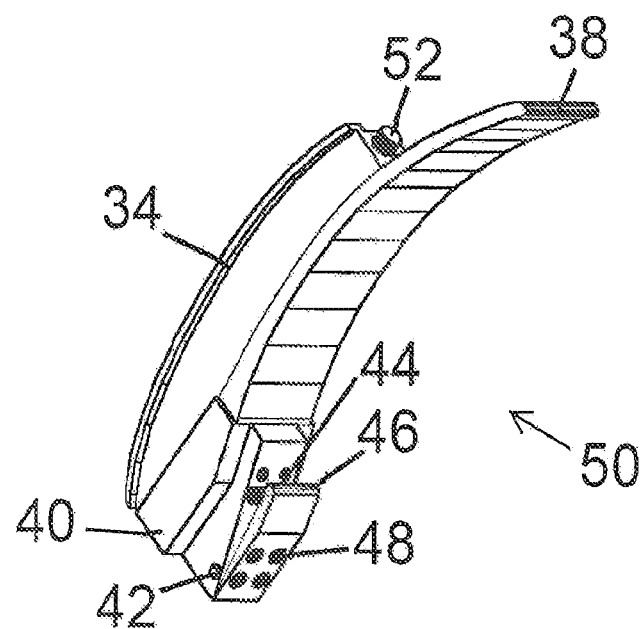
FIG. 7 is another perspective view of the standard laryngoscope blade of FIG. 6.

As shown in FIG. 6 and FIG. 7, another visualization attachment in the form of a laryngoscope blade 50 can include a similar base 40 to the laryngoscope blade 30 discussed above, but include only a light 52 integrated into the body 34 of the blade 50 and not a video camera 32. The body 34, the tip 38, and the base 40 shown in FIGS. 6 and 7 are substantially identical to those shown on blade 30 in FIGS. 4 and 5.

The light 52 can be a single large light emitting diode. The number of lights 52 is variable and equal to or greater than one. The number and strength of lights 52 is sufficient to adequately visualize the area of interest at the tip 38 of the blade 50. As shown in FIGS. 6 and 7, one embodiment of this light 52 may be a single large light emitting diode. The leads 20 on the universal base unit 10 are arranged to connect to the leads 48 on the base 40 and power the light 52 through wires that run through the base 40 and body 34 of the laryngoscope blade 50.

The laryngoscope blade 50 shown in FIGS. 6 and 7 is of comparable size to standard laryngoscope blades, and exists in adult and pediatric sizes. The geometry of the laryngoscope blade 50 may be altered while grossly maintaining a similar form.

The laryngoscope blade 50 may be made of plastic, metal, or any other sufficiently strong and rigid material. Further, the various components of the laryngoscope blade 50 can be of different materials. As shown in FIG. 8, the universal base unit 10 is connected to the laryngoscope blade 30 (alternatively, the laryngoscope blade 50 may be attached) by engaging the horizontal bar 16 of the base unit 10 with the groove 46 and the small protuberances 44 of the base 40. The assembled laryngoscope blade 30 and the base unit 10 create a single unit 80 where there is no power being transmitted to the laryngoscope blade 30 and the laryngoscope blade 30 is not in a usable position but is prepared to be modified into an engaged position, as depicted in the change in from between FIG. 8 and FIG. 9. In the orientation depicted in FIG. 8, the leads 48 on the laryngoscope blade 30 do not mate with the leads 20 on the universal base unit 10, and the hemisphere protuberances 42 do not interact with the hemisphere depressions 18 on the universal base unit 10.

In the folded position shown in FIG. 8, the unit 80 is comparable to a standard laryngoscope when a blade is connected, but not engaged. In this connected but not engaged position, the laryngoscope blade 30 may easily be adjusted into the engaged position, depicted in FIG. 9, as used in a standard laryngoscope. In the folded position, the light 36 is not powered and the video camera 32 is not powered or transmitting video to the universal base unit 10. The switch 22 may still be toggled in the folded position to create a wireless connection 26 with the wireless capable device 28 but due to the laryngoscope blade 30 not being engaged, video from the video camera 32 would not be transmitted.

As shown in FIG. 9, the laryngoscope blade 30 is moved into the engaged position such that the raised protuberances 44 engage the horizontal bar 16 and the hemisphere protuberances 42 engage the hemisphere depressions 18 on the universal base unit 10. The leads 48 on the laryngoscope blade 30 mate with the leads 20 on the universal base unit 10. In this connected and engaged position, the unit 80 is ready for clinical use.

In the engaged position, the light 36 is powered and on. The video camera 32 may receive power by default in the engaged position, or if the switch 22 is toggled. Additionally, toggling the switch 22 can enable wireless transmission 26 of video to the connected wireless device 28.

Figure 10:
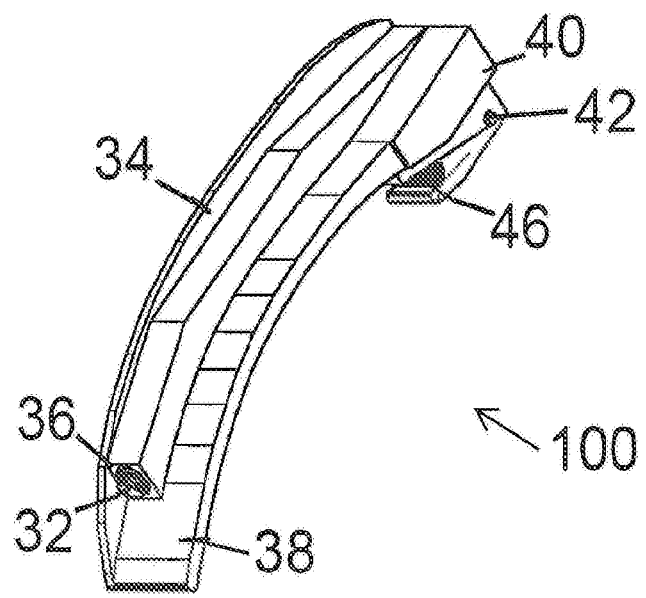
FIG. 10 is a perspective view of a visualization attachment in the form of another video laryngoscope blade with an integrated camera.
Figure 11:
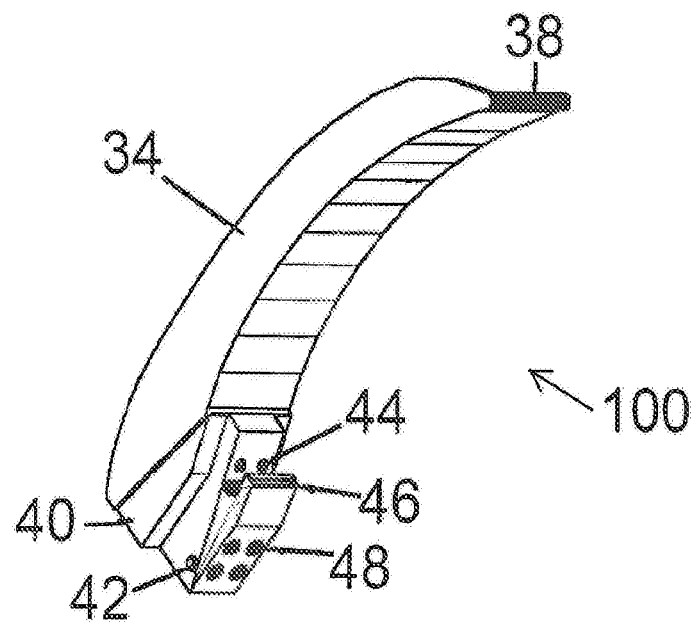
FIG. 11 is another perspective view of the video laryngoscope blade of FIG. 10.

As shown in FIGS. 10 and 11, an alternative visualization attachment in the form of a laryngoscope blade 100 with the same subcomponents of the laryngoscope blade 30 discussed above with reference to FIGS. 4 and 5. The laryngoscope blade 100 shown in FIGS. 10 and 11 includes an elongated body 34 and the video camera 32 and lights 36 are positioned closer to the tip 38 and angled in a downward trajectory toward the tip 38. Other variations with changes in position of the camera 30 and lights 36 or changes in structure of tip 38, body 34, and/or base 40 are possible, and include, but are not limited to, alternate angles of curvature and lines of the body 34.

Figure 12:
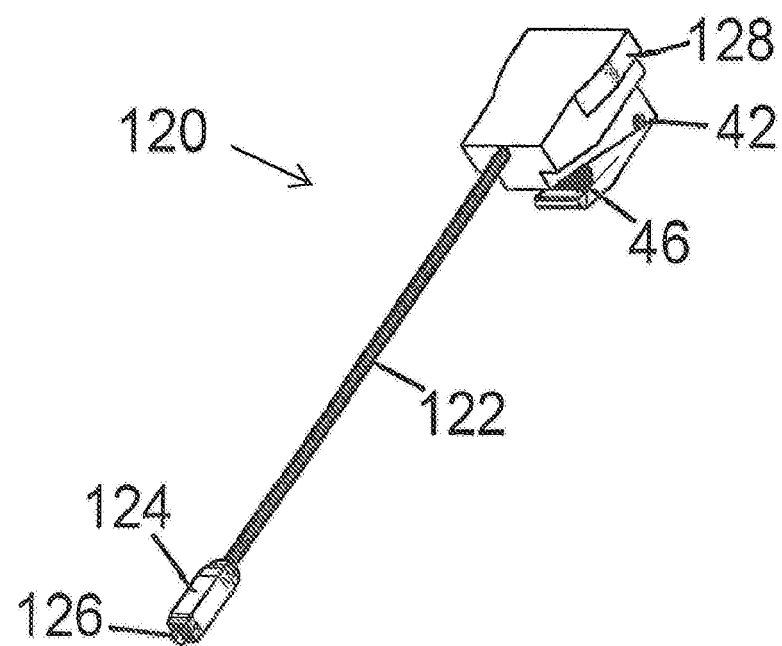
FIG. 12 is a perspective view of a visualization attachment in the form of an adhesive camera module connected to a base unit mount.
Figure 13:
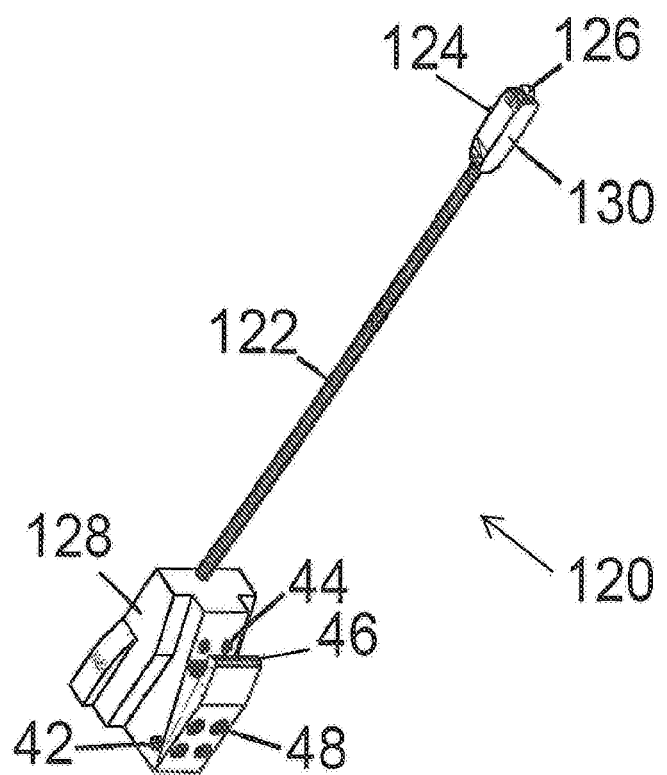
FIG. 13 is another perspective view of the adhesive camera module and the base unit mount of FIG. 12.

As shown in FIGS. 12 and 13, an alternative visualization attachment in the form of a standalone video camera component 120 that may be used to convert any laryngoscope into a video laryngoscope includes a mount 128, an insulated wire 122 to transmit power, video, and ground, and a video camera module 124.

The mount 128 of the standalone video camera component 120 utilizes the same mechanisms 44, 46 as the laryngoscope blades 30, 50 discussed above to connect to the universal base unit 10 and the same mechanism 42 as the laryngoscope blades 30, 50 to engage the universal base unit 10. The leads 48 transmit a video signal, power, and ground as in the laryngoscope blade 30. The video signal, power, and ground are transmitted to the video camera module 124 through an insulated wire 122 that also serves as a tether for the video camera module 124. The video camera module 124 contains a video camera 126. As shown in FIG. 13, a bottom surface of the video camera module 124 is covered with an adhesive material 130 that allows the video camera module 124 to be adhered to a standard laryngoscope blade.

The mount 128 of the standalone video camera component 120 is moveable between the folded position and the engaged position similar to the laryngoscope blade 30. In the engaged position, the leads 48 on the mount 128 mate with the leads 20 on the universal base unit 10, allowing power to be sent to the video camera 126 and the video signal from the video camera 126 to be sent to the electronic system 72 in the universal base unit 10 through the cap 14.

In the embodiment shown in FIGS. 12 and 13, there is no light in the video camera module 124 but the standalone video camera component 120 may optionally have one or multiple lights. The adhesive surface 130 on the bottom of the video camera module 124 has adhesive that is sufficiently strong to adhere to the surface of a laryngoscope blade made of metal, plastic, or other sufficiently strong material where it will not become dislodged under typical use while still remaining able to be removed after use. The surface 130 may also be constructed with a small magnet to be connected to a metal surface of a laryngoscope. The insulated wire 122 is of sufficient length to allow a universal base unit 10 attached to the mount 128 of the standalone video camera module 120 to be unobtrusively placed away from the site of laryngoscopy such as to the side of the patient's head. The insulated wire 122 is of sufficient strength so as to serve as a tether for the video camera module 124 to ensure that if the adhesive surface 130 should become detached from the standard laryngoscope blade, the video camera module 124 remains attached to the mount 128 through the wire 122.

The mount 128 and video camera module 124 may be made of plastic, metal, or any other sufficiently strong and rigid material. The insulated wire 122 may be made of metal covered in rubber or any other sufficiently strong and flexible material. The adhesive layer 130 on the bottom of the video camera module 124 may be made of a nontoxic, sufficiently strong adhesive that allows adhesion and removal after use, or a magnet.

Figure 14:
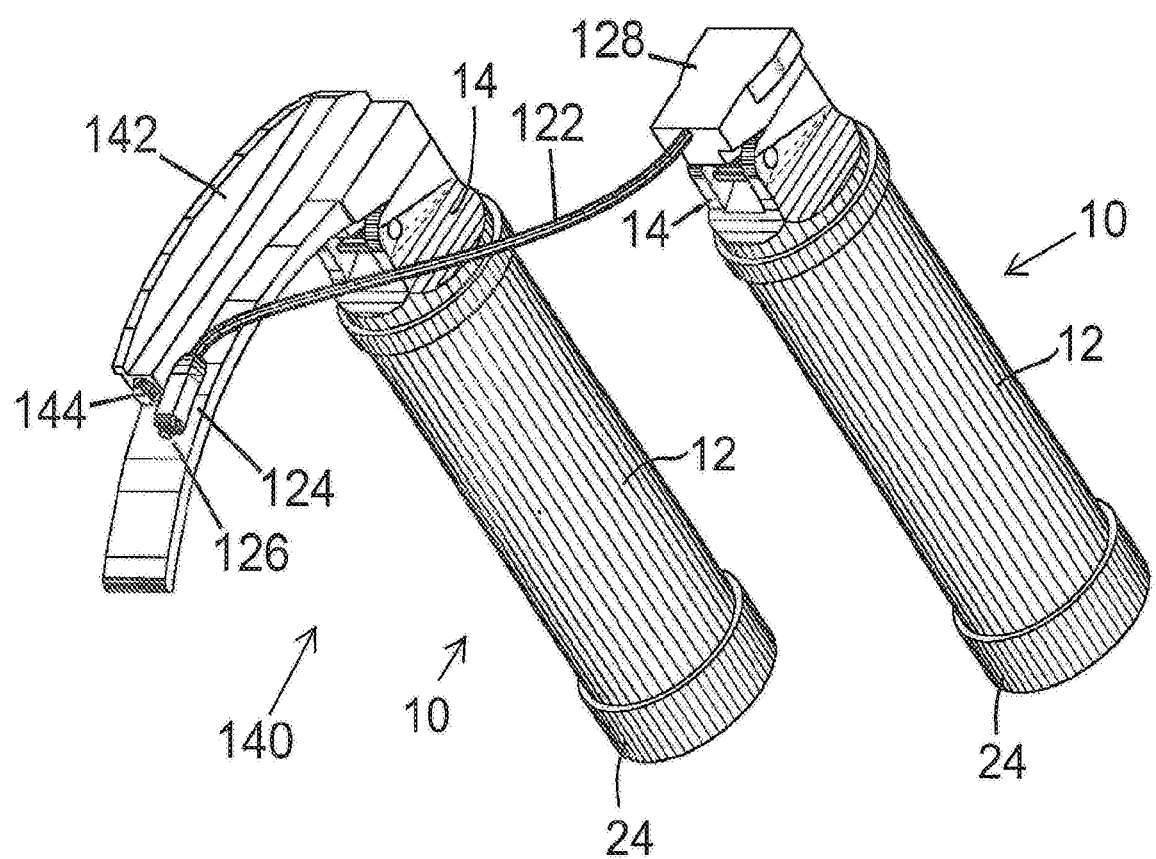
FIG. 14 is a perspective view of a base handle unit with a connected and engaged visualization attachment in the form of an adhesive camera module attached to a standard laryngoscope blade and handle.

As shown in FIG. 14, a laryngoscope 140 including a standard laryngoscope blade 142 can be coupled to the universal base unit 10 and a standalone video camera module 120 can be connected and engaged with the universal base unit 10. The video camera module 124 can then be adhered to the standard laryngoscope blade 142.

The video camera module 124 is adhered to a standard laryngoscope blade 142 utilizing the adhesive or magnet 130 that is contained on the bottom of the video camera module 124. The video camera module 124 is positioned such that it is directed toward a tip of the standard laryngoscope blade 142.

The universal base unit 10 and mount 128 of the standalone video camera component 120 are separate from the laryngoscope 140. The distance between the universal base unit 10 with the mount 128 of the standalone video camera component 120 and the laryngoscope 140 is dictated by the length of the insulated wire 122 between the mount 128 and the video camera module 124. This distance is sufficient such that the laryngoscope 140 may be used as a video laryngoscope without the universal base unit 10 and mount 128 of the standalone video camera component 120 interfering. In the embodiment demonstrated in FIG. 14, the standard laryngoscope blade 142 is connected and engaged such that light for visualization is supplied by a light 144 in the laryngoscope 140.

Figure 15:
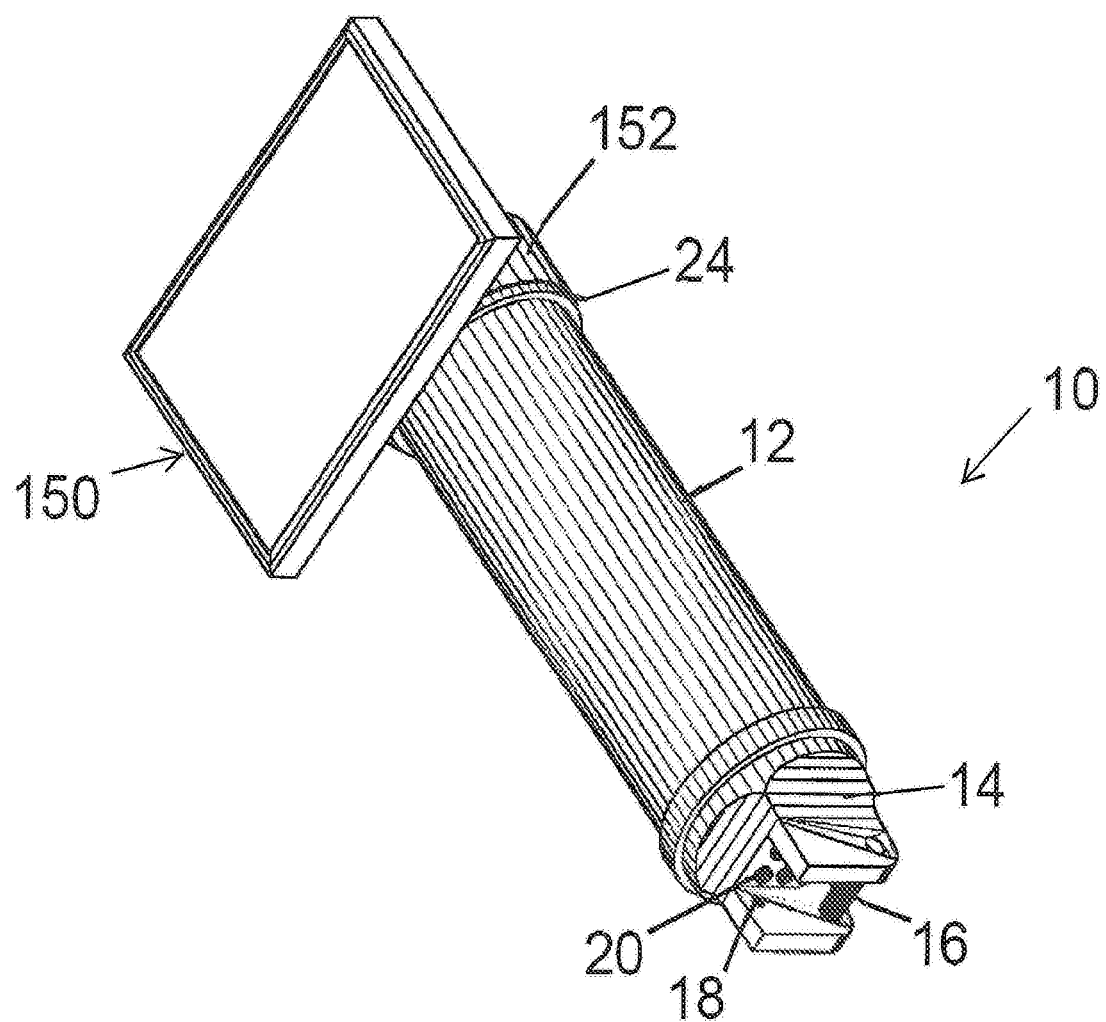
FIG. 15 is a perspective view of a base handle unit with a video display device connected.

As shown in FIG. 15, the universal base unit 10 can include a video display device 150 that directly receives a video signal from the universal base unit 10 and is connected directly to the universal base unit 10. A mount 152 attaches the video display device 150 to the universal base unit 10 and maybe formed as a part of the video display device 150.

Video from a visualization attachment is transmitted from the universal base unit 10 by direct connection to the video display device 150. The video display device 150 is either mounted on the universal base unit 10, or is separate from the universal base unit 10 but connected by a component such as a cable or wire. The video display device 150 may be a video monitor or screen or another device with a screen such as a smartphone, tablet, or personal computer. Visualization attachments connect to the universal base unit 10 as described above. In a universal base unit 10 where there is a video display device 150 that may be directly connected, there may or may not be a wireless communication chipset 152 as part of the electronic system 72. If video is being displayed on a connected video display device 150, video may or may not be additionally displayed on a wireless capable device 28 that is wirelessly connected 26 to the universal base unit 10 if a wireless communication chipset 152 is present in the electronic system 72 of the universal base unit 10.

With continued reference to FIG. 15, the video display device 150 may be permanently affixed to the universal base unit 10, or may be detachable from the universal base unit 10. The video display device 150 may be connected to the universal base unit 10 through a direct connection mechanism, such as the port or connector 54, or through a cable or wire that creates a connection between the video display device 150 and the universal base unit 10. The video display device 150 may alternately be separate from the universal base unit 10 but connected via a cable or wire. The video display device 150, if affixed to the universal base unit 10, may be capable of being adjusted in viewing angle and position to optimize viewing by the user based on the visualization attachment being used. Video may be displayed on the video display device 150 immediately when a visualization component is connected and engaged. Alternatively, the switch or button 22 on the universal base unit 10 may toggle transmission of video through the universal base unit 10 to the video display device 150.

The video display device 150 and mount 152, may be made of plastic, metal, or any other sufficiently strong and rigid material. Further, the various components of the universal base unit 10 can be made of different materials. The video display device 150 may be a video screen, monitor, or other device with a screen such as a smartphone, tablet, or personal computer. The connection between the video display device 150 and the universal base unit 10 may be a direct electronic connection, such as a port or connector 54, or an electronic connection through another component such as a wire or cable that connects to the universal base unit 10 and the video display device 150 and creates a direct electronic connection between the universal base unit 10 and the video display device 150. The wire or cable may be made of metal covered in rubber or any other sufficiently strong and flexible material.

Figure 16:
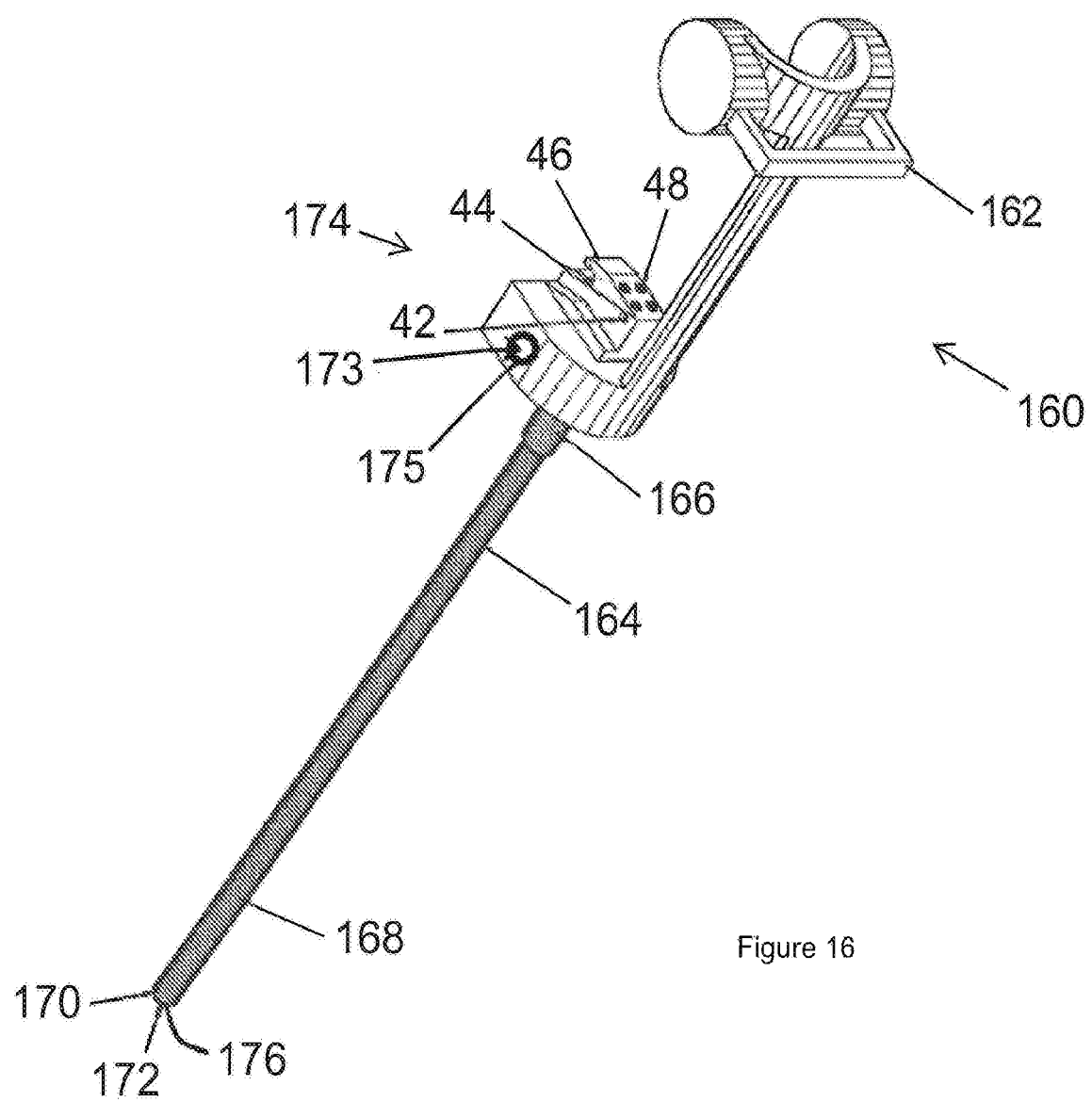
FIG. 16 is a perspective view of a visualization attachment in the form of a fiberoptic bronchoscope equivalent.

As shown in FIG. 16, a visualization attachment in the form of a fiberoptic bronchoscope equivalent 160 includes a body 174, flexible shaft 164 with a light 170 and camera 172 at a distal end, and a control mechanism 162 at a proximal end. The fiberoptic bronchoscope equivalent 160 is configured to attach to the universal base unit 10 and utilizes the same mechanisms 42, 44, and 46 as the laryngoscope blade 30 discussed above. Again, the leads 48 transmit a video signal, power, and ground as in the laryngoscope blade 30. The video signal, power, and ground are transmitted to the light 170 and the camera 172. A distal part 168 of the flexible shaft 164 may be manipulated by the control mechanism 162 present on the fiberoptic bronchoscope equivalent 160, in this embodiment depicted as a lever. Manipulation may include 2, 4, or more axis flexion/extension along with any other movement combination. There may additionally be one or more lumens 173 running through the flexible shaft 164 that each communicate between a port 175 arranged on the body 174 and a delivery port 176 arranged on the distal part 168 of the flexible shaft 164 for introducing an intervention such as providing suction, delivering oxygen, delivering drugs, and/or tool insertion.

As further shown in FIG. 16, the base 174 of the fiberoptic bronchoscope equivalent 160 has both connected and engaged functionality similar to the laryngoscope blade 30. When connected, the base 174 is secured to the universal base unit 10 through the same mechanisms 42, 44, and 46. In the engaged position, the leads 48 on the base 174 mate with the leads 20 on the universal base unit 10, allowing power to be sent to the video camera 172 and the light 170 and video signal from the video camera 172 to be sent to the electronic system 72 in the universal base unit 10 through the cap 14 and to a port or electrical connection 54 present on the universal base unit 10. There may be a segment 166 near the base 174 of larger circumference than the flexible shaft 164 of appropriate size such that an endotracheal tube may be pressure fit and held in place by the segment of larger circumference 166.

The fiberoptic bronchoscope equivalent 160, including the base 174 and control mechanism 162, may be made of plastic, metal, or any other sufficiently strong and rigid material. The flexible shaft 164 may be made of a combination of plastic, rubber, metal, or any other combination of materials that provides both strength and flexibility.

Figure 17:
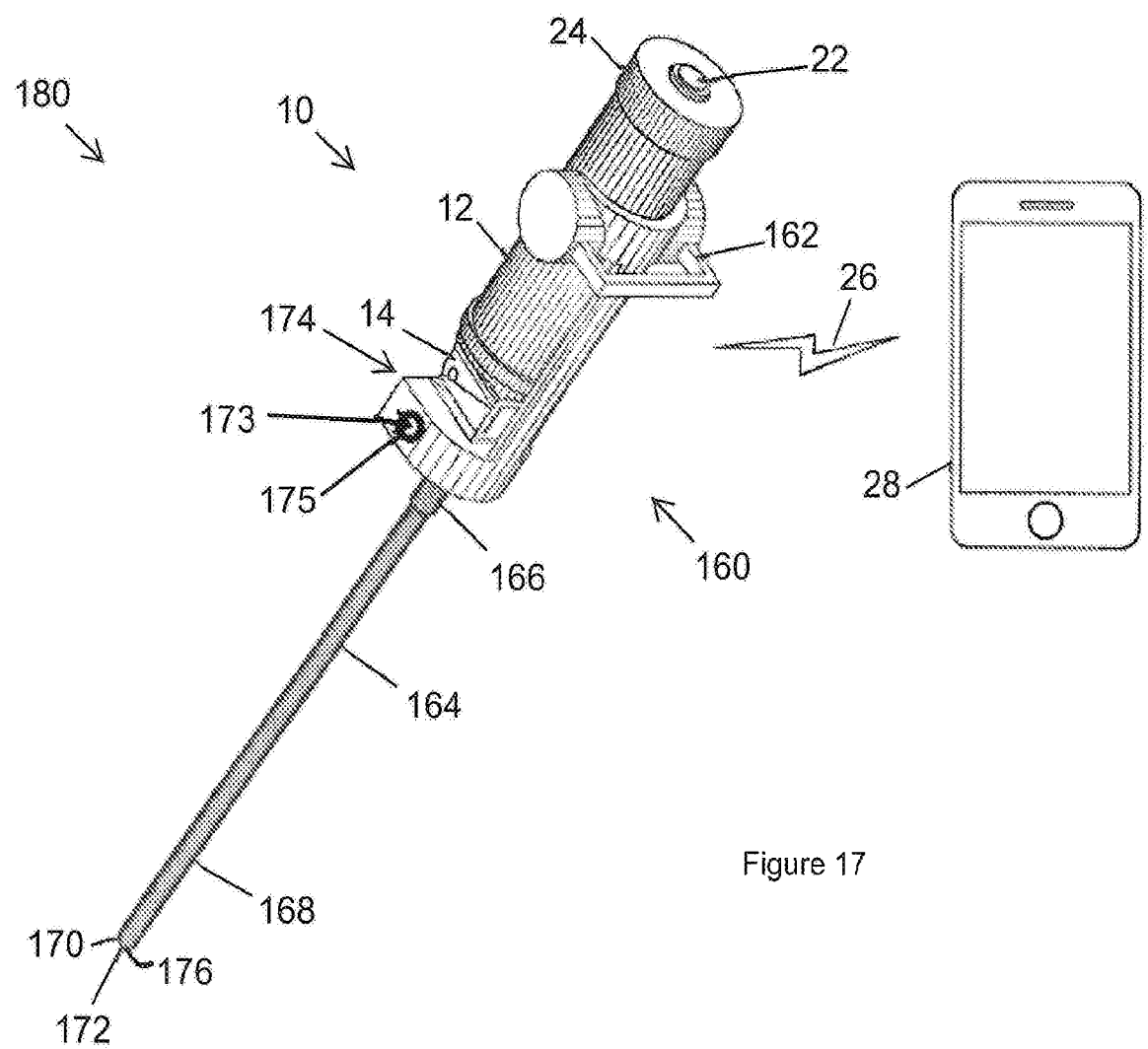
FIG. 17 is a perspective view of the fiberoptic bronchoscope equivalent of FIG. 16 connected to a base unit.

As shown in FIG. 17, the fiberoptic bronchoscope equivalent 160 can be connected and engaged to the universal base unit 10 to create a single fiberoptic bronchoscope equivalent unit 180 that may connect wirelessly 26 to the wireless capable device 28 to display video from the camera 172 of the fiberoptic bronchoscope equivalent 160 connected to the universal base unit 10. The connected and engaged unit 180 mirrors closely the standard form of a flexible bronchoscope.

Figure 18:
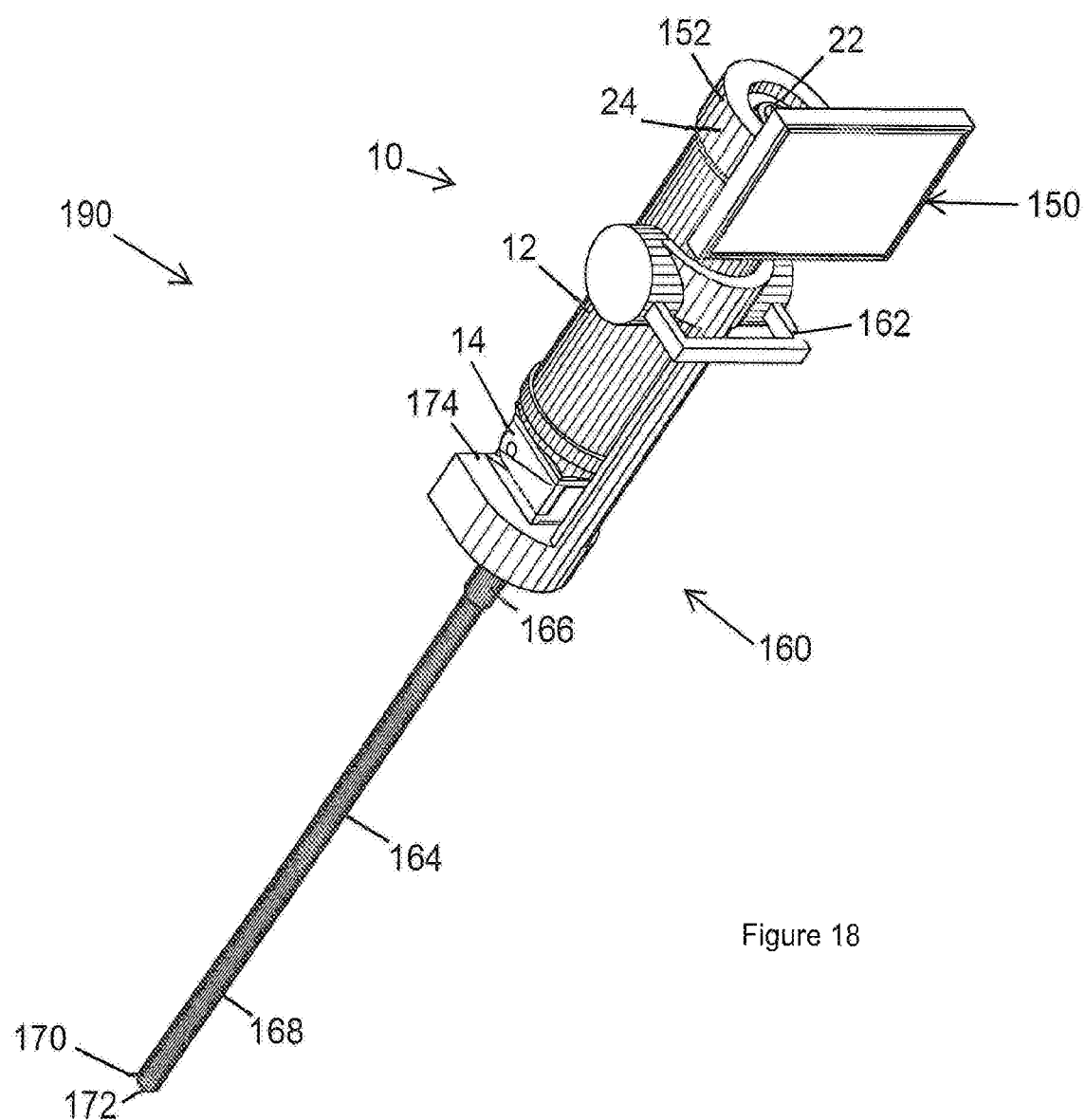
FIG. 18 is a perspective view of the fiberoptic bronchoscope equivalent of FIG. 16 connected to a base unit with an attached video display device.

As shown in FIG. 18, a fiberoptic bronchoscope equivalent 160 may be connected with a universal base unit 10 equipped with a video display device 150 to provide a complete unit 190. The fiberoptic bronchoscope equivalent 160 shown in FIG. 18 does not include the lumen 173 discussed above. In some embodiments, it may be advantageous to eliminate the lumen 173. Additionally, the lumen 173 may be included on the other visualization attachments discussed herein to allow for the introduction of an intervention on a laryngoscope blade or other visualization attachment.

As shown in FIG. 18, the light 170 and camera 172 are powered from the universal base unit 10 and video from the camera 172 is sent to the universal base unit 10 which then sends the video signal to the connected video display device 150 by way of a port or electrical connection 54, allowing for a direct connection to display the video signal from the camera 172.

Figure 19:
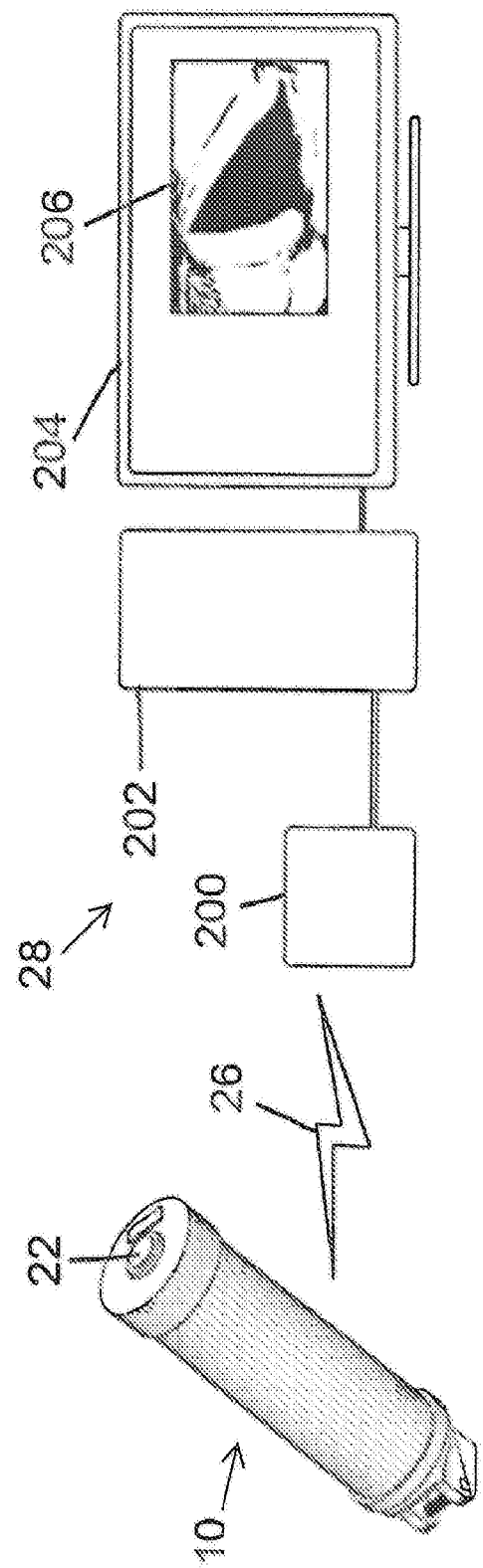
FIG. 19 is a perspective view of a base unit in communication with a computer via a network device.

As shown in FIG. 19, in one embodiment, the wireless capable device 28 includes a network device 200, a computer 202, and a monitor 204. The universal base unit 10 connects to the network device 200 through wireless communication 26 that may be triggered by the switch or button 22 on the universal base unit 10. The network device 200 is connected to or integrated into the computer 202 and allows the computer 202 to have multiple network connections. Specifically, the network device 200 is configured to receive the wireless transmission 26 from the universal base unit 10 and the computer 202 may then additionally have other network connections, wired or wireless, through other network adapters or network devices internal or external to the computer 202. The computer 202 may be specifically configured to run a hospital information system or anesthesia information management system. The computer 202 is connected to a monitor 204. The video stream from the universal base unit 10 is displayed in an app or window 206 on the monitor 204 or may be integrated into a hospital information system or anesthesia information management system. Software may run on the computer 202 such that when a wireless connection 26 is detected from the universal base unit 10, an action occurs on the computer 202 such as the app to display the video stream is launched, the app or window is maximized or brought to the front, or other such action to allow for the automatic viewing of the video stream when a wireless connection 26 is detected. In another embodiment, this action occurs when it is detected there is a non-empty video stream such as when a visualization attachment with integrated camera is connected and engaged and therefore transmitting a non-empty video stream. The app or window 206 may close, be minimized, or otherwise become hidden when the wireless connection 26 from the universal base unit 10 is disconnected or a visualization attachment with integrated camera is disengaged. This functionality allows the user to easily switch between the app or window 206 and the native hospital records or displays that normally occupy the monitor 204. Alternatively, the window 206 may be integrated into other screens or monitor display items.

Figure 20:
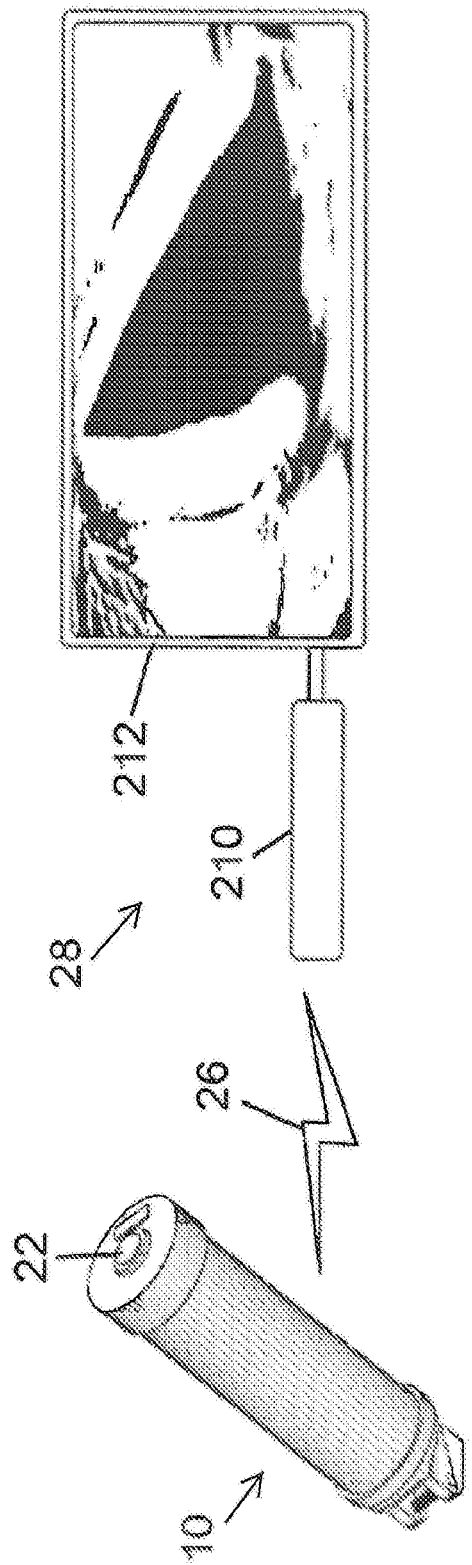
FIG. 20 is a perspective view of a base unit in communication with a monitor via a small factor computer.

As shown in FIG. 20, in one embodiment, the wireless capable device 28 includes a small form factor computer 210 with wireless connectivity that connects directly to a separate monitor or screen 212 present in the environment through a video or audio/video port, including but not limited to, HDMI, component, S-video, VGA, DVI, DisplayPort or other video or audio/video port. The small form factor computer 210 may automatically switch the input on the separate monitor or screen 212 when attached, when a wireless connection 26 is detected from the universal base unit 10 which may be activated by the button or switch 22 on the universal base unit 10, or when a non-empty video stream is detected by the small form factor computer 210 when a visualization attachment with integrated camera is connected to and engaged with the universal base unit 10. The small form factor computer 210 displays the video stream from the universal base unit 10 on the separate monitor or screen 212. The small form factor computer 210 may automatically switch the input on the separate monitor or screen 212 back to its original setting when the wireless connection 26 is disconnected or an empty video stream is detected indicating the visualization attachment with integrated camera is disengaged.

Figure 21:
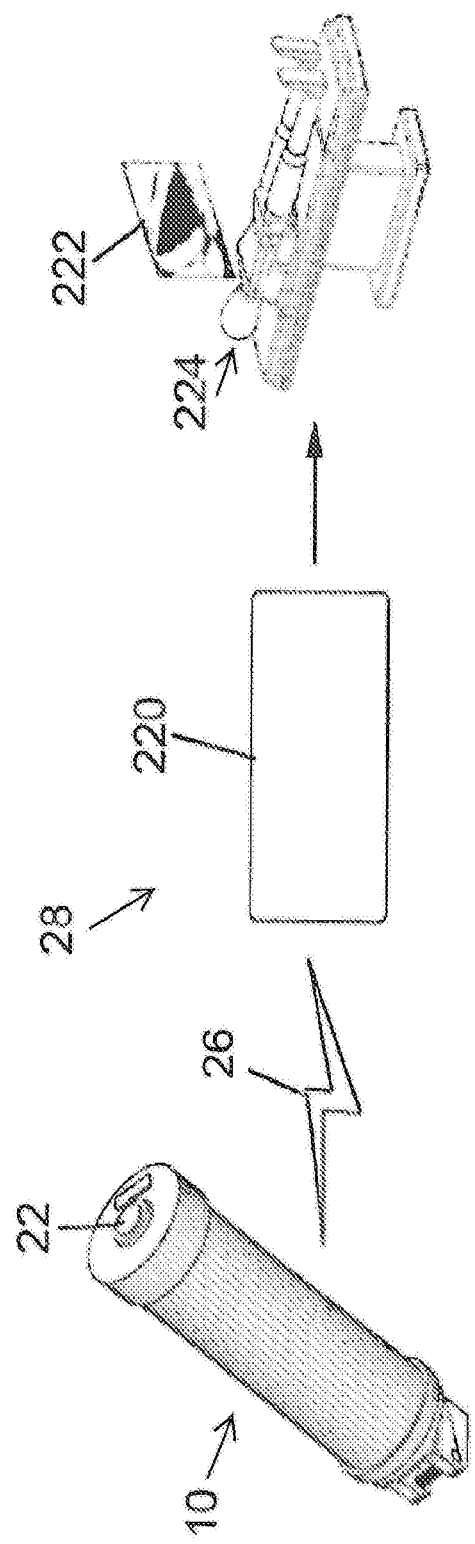
FIG. 21 is a perspective view of a base unit in communication with an augmented reality headset.

As shown in FIG. 21, in one embodiment the wireless capable device 28 includes an augmented reality headset 220 with wireless connectivity. The augmented reality headset 220 may project a virtual screen or window 222 that displays the video stream from the universal base unit 10 and may position the virtual screen or window 222 in an optimized and ergonomic position, such as above a patient 224, such that the user may view the patient and the video stream simultaneously. The augmented reality headset 220 may integrate information from other monitors or information sources and overlay or present the information beside the virtual screen or window 222 showing the video stream.

The advantages of the above embodiments must be considered in the context of acute care medicine where time, on the order of minutes to seconds, directly impacts the outcome of patient care. Acute care medical providers must adapt to rapidly changing patient condition and often request additional needed equipment for patient management in real time. Additional resources may or may not be physically available and their procurement often requires ancillary services to retrieve them from locations outside the immediate patient care location. Even if immediately available, switching from one resource to another requires physical movement of large bulky equipment, adjustment of monitors, and new connectivity. This added time, on the order of minutes to seconds, for resource procurement leads to a material delay in patient care.

The advantages of the above embodiments include, without limitation, the increased flexibility, improved workflow, and reduced time in selecting a tool for patient management, such as to assist in placement of a breathing tube. The advantages of the present invention include, without limitation, the ability for any airway provider, in any setting, to utilize video images to improve the success rate of placing a breathing tube into the patient's airway (endotracheal intubation) or other airway management. The advantages of the above embodiments also include the easy integration of the above embodiments into currently understood daily practice without changing or adding to provider workflow and reducing time delay within workflow that exists due to the inadequacies of current offerings.

The advantages of the above embodiments also relate to the familiar shape and functionality of the universal base unit, as described in the detailed description of the drawings. The universal base unit is designed to serve has a handle in most embodiments of visualization attachments and is of appropriate dimension and shape that may be gripped comfortably by a typical adult hand, specifically a roughly cylindrical shape of appropriate diameter to fit comfortably in a typical adult hand and of length roughly at least the width of a typical adult hand and not appreciably longer than a standard laryngoscope handle such that an airway expert would recognize the shape and dimension of the universal base unit as comparable to that of a standard laryngoscope handle.

The advantages of the present invention also relate to the mechanism by which a visualization attachment attaches to and engages with the universal base unit in the non-engaged and engaged position. An airway provider would readily appreciate how a visualization attachment would connect to the cylindrical bar on the universal base unit. In the preferred embodiment, the cylindrical bar is gripped by the visualization attachment, allowing rotation of the visualization attachment around the axis of the cylindrical bar from a non-engaged to engaged position. This mechanism is similar to the mechanism used by a standard laryngoscope handle and standard laryngoscope blades, and thus would be immediately recognizable by providers with airway management experience. In the case of direct laryngoscopy using the present invention, an airway provider would recognize no appreciable deviation from their standard workflow and practice. Overall, the advantages of the above embodiments include a familiar form and function for each combination of visualization attachment and universal base. An aspect of the above embodiments' uniqueness is derived from the ability to choose any of these modalities within the same device.

In consideration of video laryngoscopy, current techniques require additional bulky and expensive equipment, with limited availability or no availability in clinical settings. Time for procurement of this resource for emergent intervention, such as in the setting of an unanticipated difficult airway, leads to material delay in patient care. Furthermore, the form factor and time delay limitations are present in all current video laryngoscopy devices. The advantages of the universal base unit, serving as a handle that would be familiar to any airway provider, allow for video laryngoscopy to be seamlessly integrated in provider workflow. Furthermore, the visualization method, either wireless or wired video, would be immediately available to the provider without time delay or additional provider workflow. In emphasis, this represents an improvement in current workflow inefficiencies that are due to the limitations of current video laryngoscopy devices.

Advantages of the current device also pertain specifically to pediatric airway management due to the number and selection of laryngoscope blades required to have on hand as a result of the extremely varied airway size and anatomy in the pediatric population. The variation in pediatric airway attributes creates a unique challenge for providers managing a pediatric airway that wish to utilize video laryngoscopy; currently, different pediatric video laryngoscope sizes are only available via separate devices, creating issues of space utilization and supply management because of the large number of extra devices required to be present and available to account for the variations in pediatric airway size, attributes, and anatomy. The adhesive camera visualization attachment of the above embodiments addresses these issues by creating an airway management device that may be adhered to any pediatric laryngoscope blade to create in form and function a usable pediatric video laryngoscope. This allows video laryngoscopy to be immediately available to the pediatric airway provider, reducing time delay in patient care. Furthermore, it reduces the need for maintenance of multiple devices and space demands. Similarly, this adhesive camera visualization attachment to non-video laryngoscopes can also be used to facilitate adult video laryngoscopy.

The advantages of the above embodiments must also be discussed in the context of fiberoptic bronchoscopy, the current gold standard for airway management. Fiberoptic bronchoscopy equipment currently available is extremely bulky, requires significant planning to accommodate in an airway management setting, and is usually not available outside the operating room due to its size and expense. Thus, significant delays in obtaining fiberoptic bronchoscopy equipment occur, even during emergent situations, despite this modality being the gold standard of airway management. No device prior to the present disclosure has demonstrated utilizing a common unit between direct laryngoscopy, video laryngoscopy, and fiberoptic bronchoscopy-assisted intubation. An advantage of the above embodiments when the universal base unit is connected to and engaged with the fiberoptic-equivalent visualization attachment is that the device would immediately be recognizable by an airway provider as similar in form and function to a standard fiberoptic bronchoscope, including attributes such as where to grip and how to hold the device, where controls are located, what to expect upon manipulation of the controls, where accessory ports for irrigation/suction/tools may be located, and how to use the device for means of assisting in intubation. In one embodiment, the fiberoptic-equivalent visualization attachment would connect to the universal base unit in a manner described previously with the same mechanism used to connect a standard laryngoscope blade to a standard laryngoscope handle. While this mechanism would have no place on a traditional fiberoptic bronchoscope, and an airway provider would recognize this fact, they would immediately be familiar with the form and function of the mechanism due to their familiarity with standard laryngoscopes and when utilized, would be familiar with the resulting device appearing and functioning similarly to a standard fiberoptic bronchoscope. A further advantage of the above embodiments is the immediate availability of fiberoptic bronchoscopy and reduced space occupancy of the fiberoptic bronchoscopy unit, reducing delay in patient care and improving provider workflow.

Direct observation of the airway structures allows the provider to identify key anatomic landmarks or injury that aids in negotiating the placement of the breathing tube through the vocal cords and into the trachea. Obesity, congenital airway deformities, musculoskeletal conditions, trauma, prior surgeries or other health issues can severely alter or impact the structural or functional airway anatomy making the placement of a breathing tube difficult. Time taken for placement of the breathing tube into the trachea (on the order of minutes to seconds), repeated attempts or an unsuccessful attempt leads to significant patient morbidity and mortality. Current solutions used to visualize the airway structures require additional bulky hardware, are non-portable, have limited connectivity, include expensive components, and/or require a change in workflow that significantly limits the availability of this technology for use in airway management, especially the anticipated or unanticipated difficult airway.

The above embodiments allow the user to perform both standard (also known as "direct") and video laryngoscopy along with fiberoptic-equivalent airway management utilizing a common base unit, acting also as a handle, with a multitude of visualization attachments depending on the mode of airway management desired. The above embodiments allow the user to perform direct laryngoscopy by selecting a standard laryngoscope blade visualization attachment. The above embodiments also allow the user to perform video laryngoscopy, utilizing a wireless capable device such as a smartphone, simply by selecting a visualization attachment with integrated camera and connecting the wireless capable device to the base handle unit. Alternately, a video display device is directly connected to the handle base unit, either physically attached to the handle or separate but still physically connected through means such as a cable or wire, to display video from a connected visualization attachment with integrated camera. The user may select fiberoptic-equivalent airway management by connecting the handle base unit to the fiberoptic-equivalent visualization attachment with wireless or directly connected airway visualization as previously described. The same handle base unit is used for all endotracheal intubations in all airway management locations and the type of airway management is dependent only on the visualization attachment selected by the user. Due to the novel form factor and compact size, portability, low cost video components and easy integration into current provider workflow, the above embodiments would be available for any provider in any location where airway management occurs. As a result, this will significantly increase the availability of video assisted airway management. Furthermore, this will also increase the success rate of intubations and decrease the morbidity and mortality associated with airways that are difficult or unable to be intubated.

Another advantage of the above embodiments is the ability to convert any standard non-video laryngoscope into a video laryngoscope by using the visualization attachment with adhesive camera module. A specific advantage of this is the ability to convert any pediatric-sized blade into a pediatric video laryngoscope, for which no broadly available solution exists.

Another specific advantage of the above embodiments is the ability to convert nonstandard size laryngoscope blades, such as those used in veterinary medicine, into a video laryngoscope.

Another advantage of the above embodiments is portability and compactness, allowing this invention to be seamlessly included in operating rooms, emergency response vehicles and other airway management settings. Because the above embodiments maintains a form factor similar to long-standing laryngoscopes, no additional space is required in existing pathways, which is something no other video laryngoscopy solution may claim.

Another advantage of the above embodiments is increased connectivity, allowing for improved video and image documentation of airway management due to potential recording functionality on the wireless video monitor device. Currently, airway management is described in written form; the addition of still image or video will enhance medical documentation of airway management. The availability of video and image display in real-time will allow additional clinicians to view the airway anatomy at the same time as the clinician performing the placement of the breathing tube. As a result, team-members may more easily provide verbal or physical assistance when needed to assist the operator.

Another advantage of the above embodiments is the increased availability of fiberoptic-assisted airway management through use of the fiberoptic-equivalent visualization attachment. Fiberoptic bronchoscope carts are bulky, non-portable, and expensive and the fiberoptic component is fragile. Despite this, fiberoptic-assisted intubation remains the gold standard for truly difficult intubations and awake fiberoptic intubations are performed in known difficult airway management. The above embodiments will allow for more easily accessible and widespread deployment of fiberoptic-assisted intubation in the anticipated and unanticipated difficult airway.

Embodiments provide a medical device that is an airway visualization platform that improves the success rate of intubation by easy and rapid deployment of direct laryngoscopy, video laryngoscopy, and an equivalent of fiberoptic bronchoscopy, at the point of care and integrated into current workflow. It consists of a base unit component encasing the wireless and video encoding/processing functionality and a multitude of visualizations attachments that may be connected. In one embodiment, the base unit is a handle and the visualization attachment is a standard laryngoscope blade. In another embodiment, the base unit is a handle and the visualization attachment is a video laryngoscope blade with integrated camera. In another embodiment, the base unit is a handle and the visualization attachment is a mount that connects to the base unit with attached adhesive camera to be adhered to a separate airway management device. In another embodiment, the base unit is a handle and the visualization attachment is a component that passes through the glottic opening into the trachea with a camera integrated at its tip to provide the equivalent of fiberoptic-assisted intubation. In another embodiment, the base handle unit may be directly connected to a video display device that is physically attached to the handle or separate but still physically connected through means such as a cable or wire.

The embodiments discussed above allow direct laryngoscopy, video laryngoscopy, fiberoptic bronchoscopy (and fiberoptic bronchoscopy assisted intubation) and other modalities in any environment simply by changing the disposable visualization attachment, allowing rapid escalation of airway management with minimal delay, easy integration into existing workflow, easy integration into the out-of-OR environment.

The camera and light source being contained in a disposable visualization attachment is advantageous in that it removes restrictions in physical form of the disposable visualization attachment that would be present if the disposable part were simply a sheath or covering that fits over a single camera/light form factor. This allows further innovation of the disposable visualization attachment (like the adhesive camera) without limitation of what physical form that disposable visualization attachment would take. This also enables the device to have attachments for other areas of medicine developed (such as endoscopy for GI, urology, gynecology, etc.).

The disposable visualization attachment reduces infection transmission risk between patients between uses of the device.

While some of the above embodiments include a monitor that can attach to the top of the base unit to rapidly display the video from the base unit, one aspect of the video transmission is the use of wireless video streaming using wireless standards which diversifies the possibilities for viewing the video based on the user's need. Options include smartphones and tablets, other monitors in the environment, and the anesthesia information management system computer attached to an anesthesia machine, and even augmented reality headsets. The ability to stream video to any wireless capable device decreases the burden of additional equipment in a crowded environment and reuses screens already in the environment, whether it be the phone the anesthesiologist is carrying, the record keeping computer, or a surgical/procedure display that may be mounted somewhere in the space.

Another advantageous concept is the use of wireless standards to transmit video allowing the device to better integrate into the environment, reuse devices and screens already present in the environment, and greatly expand the possible viewing devices that can be used, including devices such as augmented reality devices.

The wireless integration allows for the ultimate use case where an anesthesia provider is performing a direct laryngoscopy and has no view, and so switches the disposable visualization attachment to the video laryngoscopy blade, turns on the base unit's wireless, and the video appears on the provider's record keeping computer's screen without any further interaction. The anesthesia provider performs the intubation and turns off the wireless, and the record keeping computer goes back to showing the record keeping software.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A medical visualization platform comprising:
   a base unit including a grip, a base unit connection mechanism, a processor, an electrical contact, a wireless communication chipset, and a power source; and
   a plurality of visualization attachments that connect to the base unit, each visualization attachment is disposable and includes a visualization connection mechanism arranged to engage the base unit connection mechanism to provide movement of the connected visualization attachment relative to the base unit between a folded position and an engaged position, each visualization attachment also includes attachment contacts that are in electrical communication with the electrical contact of the base unit while the visualization attachment is in the engaged position, and each of the visualization attachments includes either a video camera or a light source; and
   wherein the medical visualization platform is specialized for airway management and the visualization attachments comprises direct laryngoscopy blades and a fiberoptic bronchoscope equivalent;
   wherein the fiberoptic bronchoscope equivalent comprises:
      a first port;
      a flexible shaft having a delivery port on a distal end of the flexible shaft and at least one lumen in communication between the first port and the delivery port, the at least one lumen, the first port and the delivery port configured for introducing an intervention including one of delivering oxygen, delivering drugs, or tool insertion; and
      controls positioned on a proximal section of the fiberoptic bronchoscope equivalent and the controls are configured to manipulate a distal end of the fiberoptic bronchoscope equivalent, wherein when the fiberoptic bronchoscope equivalent is connected to the base unit, the controls are positioned over and overlap the grip of the base unit;
   wherein the direct laryngoscopy blades and the fiberoptic bronchoscope equivalent is secured to the base unit with the visualization connection mechanism, and utilize the same visualization connection mechanism to rotate between the folded position and the engaged position.

2. The medical visualization platform of claim 1, wherein the visualization attachments are further selected from a group consisting of video laryngoscope blades with an integrated camera, an adhesive camera module to adhere to external devices, and a fiberoptic-equivalent with an integrated camera.

3. The medical visualization platform of claim 1, wherein the medical visualization platform is specialized for endoscopy and the visualization attachments are selected from a group consisting of endoscope-equivalent modules with integrated camera specialized for endoscopy applications including esophagogastroduodenoscopy, enteroscopy, colonoscopy, sigmoidoscopy, cholangiopancreatography, rectoscopy, anoscopy, proctoscopy, rhinoscopy, pharyngoscopy, cystoscopy, ureteroscopy, and gynoscopy including colposcopy, hysteroscopy, and falloposcopy.

4. The medical visualization platform of claim 1, wherein the base unit includes a grip sized to be held by an adult human hand.

5. The medical visualization platform of claim 1, wherein the base unit power source is a battery selected from the group consisting of a replaceable non-rechargeable battery, a replaceable rechargeable battery, and a non-replaceable rechargeable battery where the rechargeable aspect may be performed external to the base unit or internal to the base unit through a physical connection or a non-physical connection.

6. The medical visualization platform of claim 5, wherein the battery is a replaceable rechargeable battery or a non-replaceable rechargeable battery and the battery is charged through inductive charging.

7. The medical visualization platform of claim 1, wherein the base unit connects to a wireless capable display device to display video from the visualization attachment.

8. The medical visualization platform of claim 1, wherein the base unit contains a port which allows for direct connection to a display device to display video from the visualization attachment.

9. The medical visualization platform of claim 1, wherein one of the visualizations attachments includes a video camera and a light source, the video camera and the light source receiving power via the attachments contacts.

10. The medical visualization platform of claim 1, wherein one visualization attachment is for pediatric use and another visualization attachment is for adult use.

11. The medical visualization platform of claim 1, wherein one visualization attachment includes a camera module connected to a connection module arranged to engage the base unit by a wire.

12. The medical visualization platform of claim 11, wherein the camera module includes an adhesive surface; and wherein the adhesive surface is configured to attach the camera module to a laryngoscope blade.

13. The medical visualization platform of claim 1, wherein the visualization attachment includes a mechanism that maintains the visualization attachment in the engaged position.

14. The medical visualization platform of claim 1, further comprising a monitor that displays video captured by one of the visualization attachments.

15. The medical visualization platform of claim 14, wherein the monitor is a monitor existing in an operating room that is enabled to communicate with the base unit.

16. The medical visualization platform of claim 14, wherein the monitor is a mobile device.

17. The medical visualization platform of claim 1, wherein the base unit communicates with an augmented reality device.

18. The medical visualization platform of claim 1, wherein one of the visualization attachments includes one or multiple lumens, each with a port for introducing an intervention and a delivery port.

\* \* \* \* \*